(12) United States Patent
Chandak et al.

(10) Patent No.: US 12,300,358 B2
(45) Date of Patent: May 13, 2025

(54) SYSTEMS AND METHODS FOR COMPRESSING GENETIC SEQUENCING DATA AND USES THEREOF

(71) Applicants: The Board of Trustees of the Leland Stanford Junior University, Stanford, CA (US); The Board of Trustees of the University of Illinois, Stanford, CA (US)

(72) Inventors: Shubham Chandak, Menlo Park, CA (US); Kedar Shriram Tatwawadi, Stanford, CA (US); Tsachy Weissman, Stanford, CA (US); Idoia Ochoa, Stanford, CA (US); Mikel Hernaez, Stanford, CA (US)

(73) Assignees: The Board of Trustees of the Leland Stanford Junior University, Stanford, CA (US); The Board of Trustees of the University of Illinois, Urbana, IL (US)

( * ) Notice: Subject to any disclaimer, the term of this patent is extended or adjusted under 35 U.S.C. 154(b) by 1421 days.

(21) Appl. No.: 16/545,751

(22) Filed: Aug. 20, 2019

(65) Prior Publication Data
US 2020/0058379 A1 Feb. 20, 2020

Related U.S. Application Data

(60) Provisional application No. 62/719,957, filed on Aug. 20, 2018.

(51) Int. Cl.
G16B 50/50 (2019.01)
G06F 16/215 (2019.01)
(Continued)

(52) U.S. Cl.
CPC ............ *G16B 50/50* (2019.02); *G06F 16/215* (2019.01); *G16B 30/10* (2019.02); *H03M 7/30* (2013.01); *H03M 7/3077* (2013.01); *H03M 7/70* (2013.01)

(58) Field of Classification Search
CPC ....... G16B 50/50; G16B 30/10; G06F 16/215; H03M 7/70; H03M 7/3077; H03M 7/30
See application file for complete search history.

(56) References Cited

U.S. PATENT DOCUMENTS

2013/0031092 A1 1/2013 Bhola et al.
2013/0204851 A1* 8/2013 Bhola ................... G16B 30/10
707/693

(Continued)

OTHER PUBLICATIONS

Ginart, Antonio A., et al. "Optimal compressed representation of high throughput sequence data via light assembly." Nature communications 9.1 (2018): 566. (Year: 2018).*

(Continued)

*Primary Examiner* — Jesse P Frumkin
(74) *Attorney, Agent, or Firm* — KPPB LLP

(57) ABSTRACT

Embodiments of the invention are generally directed to compressing genetic sequencing data. In many embodiments, the genetic sequencing data is reordered and encoded based on sequence homology between individual sequencing reads within the genetic sequencing data. Several embodiments are directed to systems to compress genetic sequencing data, and some embodiments are directed to non-transitory, machine-readable media that direct a processor to compress genetic sequencing data. In further embodiments, the genetic sequencing data represents paired-end sequencing data, and several embodiments transmit the data to a remote device.

18 Claims, 3 Drawing Sheets

(51) Int. Cl.
*G16B 30/10* (2019.01)
*H03M 7/30* (2006.01)

(56) References Cited

U.S. PATENT DOCUMENTS

| | | | | |
|---|---|---|---|---|
| 2015/0227686 A1* | 8/2015 | Sheinin | ........... | G16B 50/50 506/35 |
| 2019/0171625 A1* | 6/2019 | Leighton | ........... | G16C 10/00 |
| 2019/0214111 A1* | 7/2019 | Alberti | ........... | G06F 21/6245 |
| 2020/0043570 A1* | 2/2020 | Baluch | ........... | G06F 21/6245 |

OTHER PUBLICATIONS

Jones, Daniel C., et al. "Compression of next-generation sequencing reads aided by highly efficient de novo assembly." Nucleic acids research 40.22 (2012): e171-e171. (Year: 2012).*

Hach, Faraz, Ibrahim Numanagic, and S. Cenk Sahinalp. "DeeZ: reference-based compression by local assembly." Nature methods 11.11 (2014): 1082-1084. (Year: 2014).*

"An introduction to Next-Generation Sequencing Technology", Illumina, Inc., 2017, 16 pgs.

"Million Veteran Program", U.S. Department of Veterans Affairs, Office of Research & Development, Retrieved from: https://www.research.va.gov/mvp/, Jul. 3, 2018, 2 pgs.

"Quality Scores for Next-Generation Sequencing", Illumina, Inc., Technical Note: Sequencing, Oct. 31, 2011, 2 pgs.

"Reducing Whole-Genome Data Storage Footprint", Illumina, Inc., White Paper: Informatics, Apr. 17, 2014, 4 pgs.

"The 100,000 Genomes Project", Genomics England, 2018, Retrieved from: https://www.genomicsengland.co.uk/about-genomics-england/the-100000-genomes-project/, 4 pgs.

Bonfield et al., "Compression of FASTQ and SAM Format Sequencing Data", PLoS One, vol. 8, No. 3, e59190, Mar. 22, 2013, 10 pgs.

Chandak et al., "Compression of genomic sequencing reads via hash-based reordering: algorithm and analysis", Bioinformatics, vol. 34, No. 4, Oct. 9, 2017, pp. 558-567.

Cock et al., "The Sanger FASTQ file format for sequences with quality scores, and the Solexa/Illumina FASTQ variants", Nucleic Acids Research, vol. 38, No. 6, Dec. 16, 2009, pp. 1767-1771.

Eberle et al., "A reference data set of 5.4 million phased human variants validated by genetic inheritance from sequencing a three-generation 17-member pedigree", Genome Research, vol. 27, No. 1, Jan. 2017, pp. 157-164.

Ginart et al., "Optimal compressed representation of high throughput sequence data via light assembly", Nature Communications, vol. 9, No. 566, Feb. 8, 2018, 9 pgs.

Hach et al., "SCALCE: boosting sequence compression algorithms using locally consistent encoding", Bioinformatics, vol. 28, No. 23, Oct. 9, 2012, pp. 3051-3057.

Malysa et al., "QVZ: lossy compression of quality values", Bioinformatics, vol. 31, No. 19, May 28, 2015, pp. 3122-3129.

Numanagic et al., "Comparison of high-throughput sequencing data compression tools", Nature Methods, vol. 13, No. 12, Dec. 2016, Published Online: Oct. 24, 2016, pp. 1005-1008.

Ochoa et al., "Effect of lossy compression of quality scores on variant calling", Briefings in Bioinformatics, vol. 18, No. 2, Mar. 10, 2016, pp. 183-194.

Roguski et al., "DSRC 2—Industry-oriented compression of FASTQ files", Bioinformatics, vol. 30, No. 15, Aug. 1, 2014, pp. 2213-2215.

Roguski et al., "FaStore: a space-saving solution for raw sequencing data", Bioinformatics, vol. 34, No. 16, Aug. 15, 2018, pp. 2748-2756.

Alberti et al., "An introduction to MPEG-G, the new ISO standard for genomic information representation", bioRxiv, vol. 426353, Oct. 8, 2018, pp. 1-18.

Long et al., "GeneComp, a New Reference-Based Compressor for SAM Files", 2017 Data Compression Conference (DCC), Apr. 4-7, 2017, 13 pgs.

* cited by examiner

SYSTEMS AND METHODS FOR COMPRESSING GENETIC SEQUENCING DATA AND USES THEREOF

CROSS REFERENCE TO RELATED APPLICATIONS

This application claims priority to U.S. Provisional Application Ser. No. 62/719,957 entitled "Systems and Methods for Compressing Genetic Sequencing Data" to Chandak et al., filed Aug. 20, 2018, which is incorporated herein by reference in its entirety.

STATEMENT REGARDING FEDERALLY SPONSORED RESEARCH OR DEVELOPMENT

This invention was made with Governmental support under Grant No. 5U01CA198943-03 awarded by the National Institutes of Health. The government has certain rights in the invention.

FIELD OF THE INVENTION

The present invention is directed to genetic sequencing data, including methods of compressing and decompressing genetic sequencing data, more particularly, methods to compress and decompress that involve reordering and encoding individual reads within the genetic sequencing data.

BACKGROUND OF THE INVENTION

High-Throughput Sequencing technologies produce huge amounts of data in the form of short genomic reads, associated quality values and read identifiers. Because of the significant structure present in these FASTQ datasets, general-purpose compressors are unable to completely exploit much of the inherent redundancy. Although there has been a lot of work on designing FASTQ compressors, most of them lack in support of one or more crucial properties, such as support for variable length reads, scalability to high coverage datasets, pairing-preserving compression and lossless compression.

SUMMARY OF THE INVENTION

Systems and methods for application identification in accordance with embodiments of the invention are disclosed. In one embodiment, a method for compressing genetic sequencing data includes obtaining genetic sequencing data containing a plurality of sequencing reads, reordering a subset of the plurality of sequencing reads from the genetic sequencing data based on homology between sequencing reads in the subset of the sequencing reads, encoding the subset of sequencing reads by generating a reference sequence, where each sequencing read in the subset of sequencing reads aligns to the reference sequence at a position, and the position of each sequencing read in the subset of sequencing reads creates an order of sequencing reads in the subset of sequencing reads, reordering the plurality sequencing reads by generating a plurality of data streams describing characteristics about each sequencing read in the plurality of sequencing reads, where each sequencing read in the subset of sequencing reads is reordered based on its order in the subset of sequencing reads and includes its position in the reference sequence, and compressing the reordered plurality of sequencing reads.

In a further embodiment, the compressing step is performed in a series of blocks representing a second subset of sequencing reads in the plurality of sequencing reads.

In another embodiment, the genetic sequencing data represents paired-end sequencing data containing a plurality of paired sequencing reads, where each pair of sequencing reads contains a first read and a second read, where the first read represents one end of a sequenced molecule, and the second read represents an opposite end of the sequenced molecule.

In a still further embodiment where the genetic sequencing data represents paired-end sequencing data, the method further includes reordering and encoding a subset of second reads of the plurality of paired sequencing reads, where each second read in the subset is reordered based on the order of its paired first read and includes its position relative to the paired first read.

In still another embodiment, the method includes transmitting the compressed reordered plurality of sequencing reads to a remote device.

In a yet further embodiment, the genetic sequencing data includes quality data for each sequencing read in the plurality of sequencing reads.

In yet another embodiment where the genetic sequencing data includes quality data, the method includes reordering the quality data, where the quality data is reordered based on the order of its respective sequencing read.

In a further embodiment again, a system for compressing genetic sequencing data includes a processor, a memory readable by the processor, and instructions in the memory that when read by the processor direct the processor to obtain genetic sequencing data containing a plurality of sequencing reads, reorder a subset of the plurality of sequencing reads from the genetic sequencing data based on homology between sequencing reads in the subset of the sequencing reads, encode the subset of sequencing reads by generating a reference sequence, where each sequencing read in the subset of sequencing reads aligns to the reference sequence at a position, and the position of each sequencing read in the subset of sequencing reads creates an order of sequencing reads in the subset of sequencing reads, reorder the plurality sequencing reads by generating a plurality of data streams describing characteristics about each sequencing read in the plurality of sequencing reads, where each sequencing read in the subset of sequencing reads is reordered based on its order in the subset of sequencing reads and includes its position in the reference sequence, and compress the reordered plurality of sequencing reads.

In another embodiment again, the instructions further direct the processor to compress the plurality of sequencing reads in a series of blocks representing a second subset of sequencing reads in the plurality of sequencing reads.

In a further additional embodiment, the genetic sequencing data represents paired-end sequencing data containing a plurality of paired sequencing reads, where each pair of sequencing reads contains a first read and a second read, where the first read represents one end of a sequenced molecule, and the second read represents an opposite end of the sequenced molecule.

In another additional embodiment where the genetic sequencing data represents paired-end sequencing data, the instructions further direct the processor to reorder and encode a subset of second reads of the plurality of paired sequencing reads, where each second read in the subset is reordered based on the order of its paired first read and includes its position relative to the paired first read.

In a still yet further embodiment, the instructions further direct the processor to transmit the compressed reordered plurality of sequencing reads to a remote device.

In still yet another embodiment, the genetic sequencing data includes quality data for each sequencing read in the plurality of sequencing reads.

In a still further embodiment again where the genetic sequencing data includes quality data, the instructions further direct the processor to reorder the quality data, where the quality data is reordered based on the order of its respective sequencing read.

In still another embodiment again, a non-transitory, machine-readable medium containing processor instructions, where execution of the instructions by a processor causes the processor to perform a process to compressing genetic sequencing data includes obtaining genetic sequencing data containing a plurality of sequencing reads, reordering a subset of the plurality of sequencing reads from the genetic sequencing data based on homology between sequencing reads in the subset of the sequencing reads, encoding the subset of sequencing reads by generating a reference sequence, where each sequencing read in the subset of sequencing reads aligns to the reference sequence at a position, and the position of each sequencing read in the subset of sequencing reads creates an order of sequencing reads in the subset of sequencing reads, reordering the plurality sequencing reads by generating a plurality of data streams describing characteristics about each sequencing read in the plurality of sequencing reads, where each sequencing read in the subset of sequencing reads is reordered based on its order in the subset of sequencing reads and includes its position in the reference sequence, and compressing the reordered plurality of sequencing reads.

In a still further additional embodiment, the compressing step is performed in a series of blocks representing a second subset of sequencing reads in the plurality of sequencing reads.

In still another additional embodiment, the genetic sequencing data represents paired-end sequencing data containing a plurality of paired sequencing reads, where each pair of sequencing reads contains a first read and a second read, where the first read represents one end of a sequenced molecule, and the second read represents an opposite end of the sequenced molecule.

In a yet further embodiment again where the genetic sequencing data represents paired-end sequencing data, the instructions further include reordering and encoding a subset of second reads of the plurality of paired sequencing reads, where each second read in the subset is reordered based on the order of its paired first read and includes its position relative to the paired first read.

In yet another embodiment again, the instructions further include transmitting the compressed reordered plurality of sequencing reads to a remote device.

In a yet further additional embodiment, the genetic sequencing data includes quality data for each sequencing read in the plurality of sequencing reads.

BRIEF DESCRIPTION OF THE DRAWINGS

These and other features and advantages of the present invention will be better understood by reference to the following detailed description when considered in conjunction with the accompanying drawings where.

DETAILED DISCLOSURE OF THE INVENTION

Figure 1:
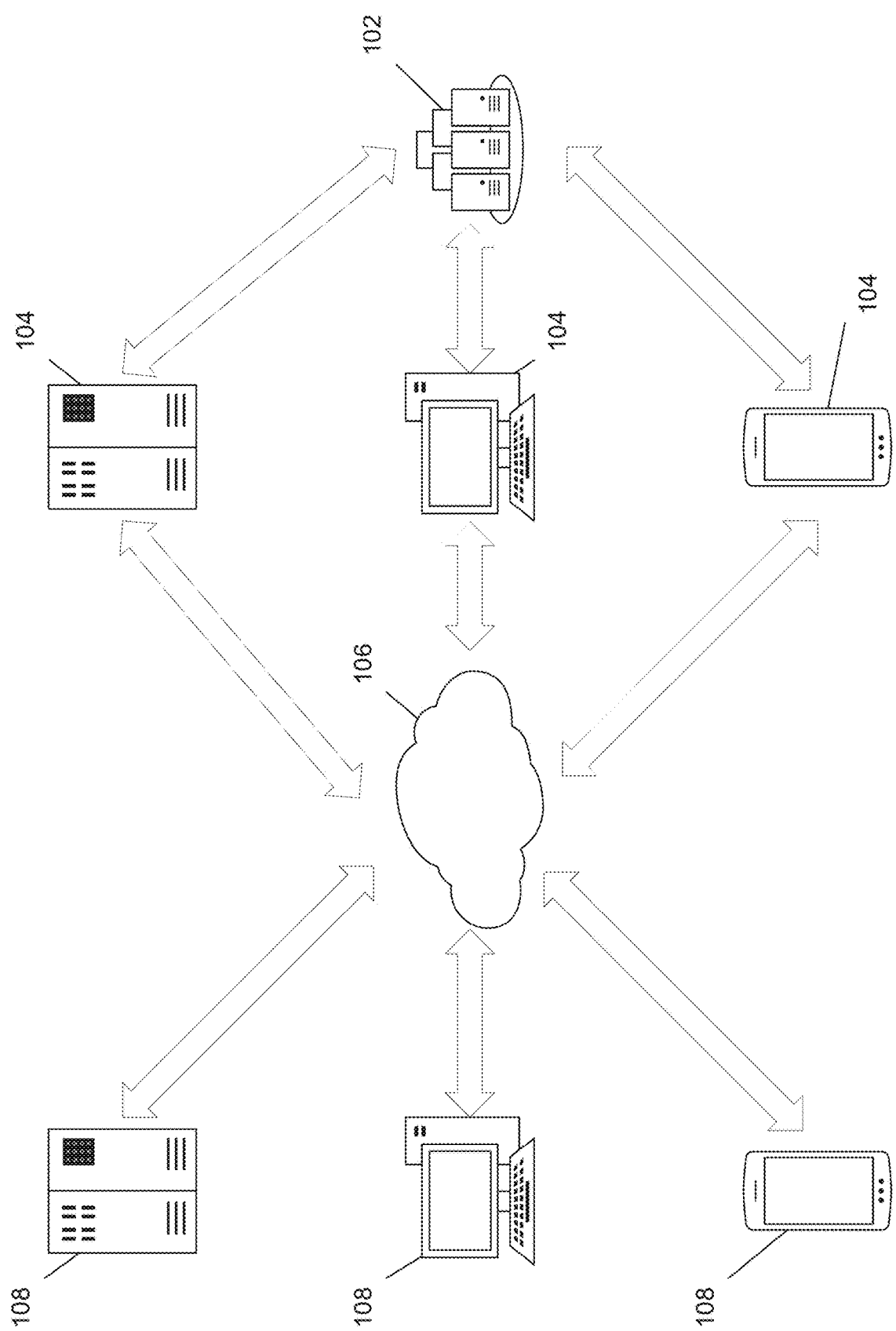
FIG. 1 illustrates a system architecture for compressing and/or transmitting genetic sequencing data in accordance with various embodiments.

There has been a tremendous increase in the amount of genomic data produced in the past few years, mainly driven by the improvements in High-Throughput Sequencing technologies and the reduced cost of sequencing a genome. A single genome sequencing experiment on humans typically results in hundreds of millions of short reads (of length 100-150 bp), which are (possibly corrupted) substrings of the same underlying genome sequence. These raw sequencing data is typically stored in the FASTQ format, which consists of the reads along with the quality values which indicate the confidence in the read sequence and read identifiers which consist of metadata related to the sequencing process. In most cases, the reads are sequenced in pairs from short fragments of the genome, resulting in paired-end FASTQ files. A typical FASTQ dataset for a human genome sequencing experiment requires hundreds of GBs of storage space (for a typical sequencing coverage of 30×). Due to the huge sizes involved, compression of the FASTQ files is of utmost importance for their storage and distribution.

There is significant amount of recent work on FASTQ compression, including SCALCE, Fqzcomp, DSRC 2, and FaStore. See e.g., Numanagic, et al., (2016) Comparison of high-throughput sequencing data compression tools. Nat. Methods, 13, 1005; Hach, et al., (2012) SCALCE: boosting sequence compression algorithms using locally consistent encoding. Bioinformatics, 28, 3051-3057; Bonfield and Mahoney, (2013) Compression of FASTQ and SAM format sequencing data. PLoS One, 8, e59190; Roguski, et al. (2018) Fastore: a space-saving solution for raw sequencing data. Bioinformatics, 34, 2748-2756; and Roguski and Deorowicz, (2014) DSRC 2-industry-oriented compression of FASTQ files. Bioinformatics, 30, 2213-2215; the disclosures of which are incorporated by reference in their entirety.) Since the reads are sub-strings of the underlying genome, there is much redundancy to be exploited for compression. Specialized compressors, which explicitly utilize the structure present in the reads, can achieve a compression gain of more than 10× as compared to generic universal compressors such as Gzip. The quality values, on the other hand, have less structure and thus can take up a more significant fraction of the storage space in the compressed domain. Recent work has shown that the quality values can be lossily compressed without adversely affecting the performance of variant calling, one of the most widely used downstream application in practice. (See e.g., Ochoa, et al. (2017) Effect of lossy compression of quality scores on variant calling. Brief. Bioinform., 18, 183-194; the disclosure of which is incorporated by reference in its entirety.) Moreover, newer technologies such as Illumina's NovaSeq are using quality values with fewer levels (4 levels instead of the previous 8 or 40 levels), hence supporting the claim that the precision in the quality values can be reduced with no impact on variant calling performance.

Although there has been a lot of work on designing FASTQ compressors, most of them lack in support of one or more crucial properties, such as support for variable length reads, scalability to high coverage datasets, pairing-preserving compression and lossless compression. Partly due to these factors, Gzip is still the prevalent FASTQ compressor, even though it provides worse compression ratios.

Turning now to the drawings and figures, systems and methods for compressing genetic sequencing data and uses thereof in accordance with embodiments of the invention are illustrated. In a number of embodiments, an application on a computing device such as (but not limited to) a server, desktop computer, laptop, mobile phone and/or tablet computer is used to compress genetic sequence data generated by a sequencing platform, including raw sequencing reads and/or quality information. In many embodiments, the genetic sequence data comprises sequencing read information, such as raw sequencing reads and/or quality information for the sequencing reads. Many embodiments will compress sequencing data in the form of raw sequencing reads, such as data contained within a FASTA or a FASTQ file. Certain embodiments will allow for perfect reconstruction of the sequencing data, including read order contained within input sequencing data, while some embodiments will reorder sequencing data in a minimally lossy compression.

Turning to FIG. 1, a generalized architecture for generating and compressing genetic sequencing data is illustrated. In many embodiments, a sequencing platform 102 generates sequencing data from input nucleic acids (e.g., DNA or RNA). Numerous sequencing platforms are known in the art, including sequencing platforms manufactured by Illumina, Roche, IonTorrent, Pacific Biosciences, Helicos, Applied Biosystems (ABI), and/or Oxford Nanopore, including Illumina's MiSeq, HiSeq, HiScan, NovaSeq, MiniSeq, and/or NextSeq, Roche's 454 platforms, IonTorrent's PGM and/or Proton, Pacific Biosciences RS and/or Sequel, Helicos's Heliscope, ABI's 3700 platforms, and/or Oxford Nanopore's MinION, GridION, and/or PromethION. Many embodiments will produce genetic sequencing data in the form of just sequencing reads (e.g., FASTA format) or sequencing reads with quality data (e.g., FASTQ format). Many sequencing platforms produce paired-end sequencing data, where each molecule sequenced by the sequencing platform is sequenced from each end of the molecule. Additionally, some sequencing platforms produce variable length reads (e.g., individual reads from a single run can vary in length), while some platforms produce reads with a specified length (e.g., all reads from a single run have the same length).

In a number of embodiments, the genetic sequencing data is maintained locally on the sequencing platform 102, while certain embodiments will transfer the genetic sequencing data to one or more computing devices 104, such as servers, personal computers, mobile devices and/or any other adequate computing device. Many times, genetic sequencing data needs to be shared with collaborators, medical professionals, or for secure storage (e.g., off-site backups). In embodiments that share the genetic sequencing data, the genetic sequencing data will be transmitted across one or more networks 106 to remote devices 108, such as servers, personal computers, mobile devices and/or any other adequate computing device.

Sequencing platforms can generate vast quantities of data, such that a single sequencing run can generate upwards of 6 trillion base pairs of data, which translates to terabytes of data. The raw sequencing reads need to be saved and stored for many projects to allow for reanalysis of the sequencing reads, such as when a sequencing run represents a specific time point and/or as analytical methods or references improve. Due to the large amounts of data generated, the ability to save and/or transfer genetic sequencing data becomes difficult and/or expensive. For example, purchasing and shipping hard drives becomes expensive and/or inefficient to access the data. Additionally, data transfer and/or access costs increase dramatically with the amount of data and people needing to access the data. As such, a need exists in the art to be able to compress genetic sequencing data as much as possible in order to transfer more data in a shorter amount of time as well as for a lower cost.

Sequence Data Compression

Figure 2:
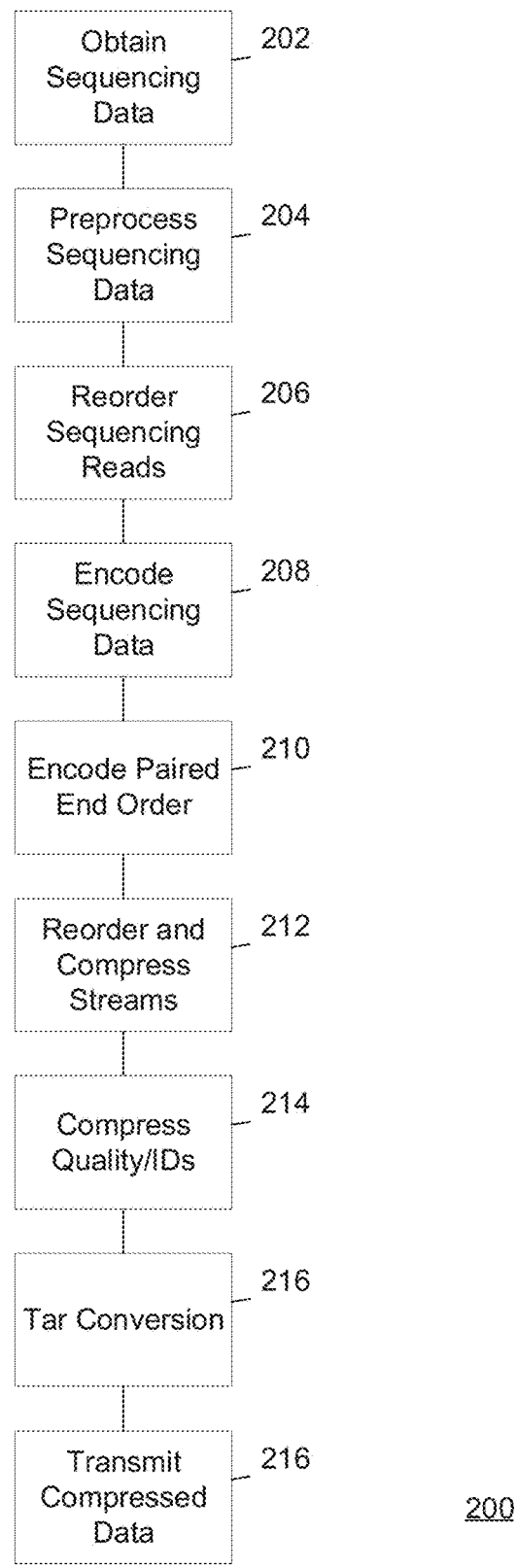
FIG. 2 illustrates a method for compressing genetic sequencing data in accordance with various embodiments.

Turning now to FIG. 2, a method 200 of compressing genetic sequencing data is illustrated. At Step 202, genetic sequencing data is obtained in many embodiments. Genetic sequencing data in a number of embodiments will comprise a plurality of sequencing reads. In certain embodiments, the reads are associated with read identifiers and/or quality information (e.g., quality scores). In various embodiments, the genetic sequencing data is obtained directly from a sequencing platform, such those described herein. A number of embodiments will obtain sequencing data from a secondary source, such as shared data from public resources and/or individuals. Further embodiments will obtain simulated data that has artificially created to test certain platforms and/or algorithms. Many embodiments will obtain the sequencing data in the form of sequencing reads (e.g., FASTA format), which may also include quality data associated with the sequencing reads (e.g., FASTQ format). Many embodiments are capable of compressing sequencing data from single or paired-end sequencing, thus many embodiments will obtain paired-end sequencing data. Paired-end sequencing data describes paired reads containing a first read and a second read for each sequenced molecule, where the first read represents one end of a sequenced molecule, and the second read represents the opposite end of the sequenced molecule. In many platforms, paired-end sequencing data is generated from a sequencing platform in the form of two files, where a first file contains the first reads for individual molecules to be sequenced, and a second file represents the second, or paired, reads representing the other end of the same molecule.

A number of embodiments will preprocess genetic sequencing data at Step 204. In many embodiments, preprocessing Step 204 will separate individual sequencing reads in the genetic sequencing data from the other information within the genetic sequencing data (e.g., read identifiers and/or quality data).

Many embodiments will reorder sequencing data at Step 206. During reordering of many embodiments, the sequencing reads within the sequencing data are aligned based on homology between sequencing reads within the sequencing data. By aligning sequencing reads, the order of reads is changed to the relative position between sequences. In a variety of embodiments, aligning sequencing reads is performed in an iterative manner, whereby given an individual sequencing read, these embodiments will attempt to identify another read that matches either a prefix or suffix sequence of the individual read with a small Hamming distance. By looking for matching reads that match the prefix or suffix of the individual read, reordering is performed bidirectionally, rather than unidirectional methods that only identify subsequent reads that only match a suffix of the individual read. In many of these embodiments, a hash table is used to index reads according to substrings located within the read (e.g., a prefix of a read can be used as a hash table location, and the remainder of the read is stored within the hash table). Additional embodiments will allow for variable read length, which will utilize an array containing read lengths to ensure that hamming distances between reads are computed correctly. It should be noted that many times, sequences will not align to a reference sequence and will be noted an unaligned.

Further embodiments will stop the reordering step without completely aligning all reads within the sequence data. Early stopping produces a time advantage in compression, because many reads will not align due to a lack of homology with other sequences within the sequencing data as a whole or a block of sequencing data. To avoid time looking iteratively for similar reads, many of these embodiments will set an early stopping threshold, which will stop reordering sequencing reads, once the threshold is passed. For example, many embodiments will set a 50% threshold for unmatched reads, which will stop reordering once 50% of the reads have been aligned and reordered. In additional embodiments, the threshold is measured in a rolling interval, where if a specific threshold is not met over the course of the interval, reordering stops. For example, if a threshold is set to 50% with an interval of 1 million reads, if less than 50% of the most recent 1 million reads aligned, reordering stops.

In many embodiments, the sequencing data is encoded at Step 208. In these embodiments, the sequences of reordered reads are used to construct a reference sequence (e.g., a contig). The final encoding in certain embodiments will comprise the reference sequence, the positions of the reads in the reference sequence, and the mismatches of reads with respect to the reference sequence. In additional embodiments, an index mapping the reordered reads to their position in the original sequencing data (e.g., FASTA or FASTQ file) is also generated. In some embodiments where the order of the sequencing reads is not preserved, the position of sequencing reads is a position relative to the previous read, rather than a specific position relative to the reference sequence. Unaligned sequencing reads will be stored separately in certain embodiments.

When compressing paired-end sequencing data, numerous embodiments will reorder the sequences and encode the paired-end sequencing reads at Step 210. In some embodiments, this step is only performed when the order of reads is not preserved in the process, versus embodiments that preserve the order of sequencing reads. A number of embodiments will generate an index that maps the reordered paired-end sequencing reads to the position of the previously reordered reads (e.g., reads reordered in Steps 206 and 208). In embodiments that reorder and encode the paired-end reads, the reads representing the paired end are placed in the same order as the first set of reads. By keeping the paired-end reads in the same order as the first-end reads, no additional data is necessary to identify which read represents the paired read to its respective first-end read. Additionally, position of the paired-end read can be encoded as its position relative to its correlated first-end read.

At Step 212 of many embodiments, a plurality of read streams (described below) are generated, then reordered, and compressed. In embodiments that preserve the original order of sequencing reads, the streams are ordered according to the original order of reads in the obtained genetic sequencing data, while in embodiments that do not preserve read order, the data streams are reordered based on the order generated in the encoding Steps (e.g., Step 208 and/or Step 210). Various embodiments will utilize known compression methods, including BSC, to compress the reordered data streams. As genetic sequencing data can contain millions or billions of individual sequencing reads, which can be onerous for a computing system to process in a single block. As such, certain embodiments will compress the streams in a series of blocks comprising a set number of reads, which is less than the total number of reads in the sequencing data. As such, many embodiments will elect block sizes of between 10,000 and 1,000,000 sequencing reads within a block. Some embodiments will automatically determine optimal block size based on sequencing read length within the sequencing data, while certain embodiments will allow a user to select block size. For example, long read lengths can be placed into block sizes of 10,000 reads, while short read lengths can be placed into blocks of 100,000, 256,000, or 1,000,000 reads per block. In embodiments performing compression of paired-end sequencing data with two files (where each file represents a read from each end of a sequencing molecule), a block of sequences is taken from each file, where the sequencing read data in each block represent sequencing reads from the same molecule (e.g., the sequencing reads in each block are the paired-ends from the same sequencing molecules). In some of the embodiments of paired-end sequencing, the blocks from the first and second reads are concatenated as a single file.

Data streams that will be utilized in various embodiments include the data streams listed below. While the list of data streams can be used in embodiments. Certain embodiments will not utilize all data streams (e.g., embodiments only storing single read data will not generate data regarding paired-end sequencing data). Additionally, many embodiments can generate and utilize further data streams not described herein.

Sequence: The constructed reference sequence.

Flag: An indicator of whether individual reads were aligned to the reference sequence, and in paired-end sequencing, whether the first and second reads have a gap above a specific threshold. For example, flags in single read sequencing data can indicate whether the read aligned to the reference sequence or whether the read did not align to the reference sequence. In paired-end sequencing data, the flag can indicate whether the first read, the second read, or both reads align to the reference sequence. Additionally, in paired-end sequencing data, when both sequences align to the reference sequence, the flag can indicate whether the gap distance between the aligned reads is above or below a certain threshold.

Position: the position of sequencing reads.
  Embodiments preserving sequence read order: In single read sequencing data, the positions of the reads can be stored for the aligned sequencing reads. In paired-end sequencing data, the position of the first aligned read can be stored. In situations where paired sequencing reads have a gap distance above a specified threshold, the positions of both reads can be stored.
  Embodiments that do not preserve sequence read order: In single read sequencing data, the positions can be stored as the difference between the position of a read and the position of the previous read. In paired-end sequencing data, the positions can be stored as the difference between the position of a first read of a particular pair and the position of the first read of a previous pair. By storing only differences rather than absolute positions, smaller amounts of data are required to encode positional information. In paired-end sequencing data, the position of the first aligned read can be stored. In situations where paired sequencing reads have a gap distance above a specified threshold, the positions of both reads can be stored.

Paired Position: the position of the second read from paired-end sequencing data representing the difference in the position of the second read of a pair to the first read of the same pair. Paired reads are typically within a limited distance to each other (e.g., 50-250 base pairs). Storing second read position relative to the first read exploits these relatively small numbers to allow the storing of smaller amounts of data.

Noise: information on "noisy" bases within a sequencing read, where noise can be stored based on transition probability. Certain sequencing platforms have non-random error rates, and storing noisy bases based on transition probability can exploit the likely transitions to reduce the amount of data being compressed.

Noisy position: position of noisy bases in a noise stream. The position can be stored as a relative position (e.g., relative to the first base of a particular sequencing read) to limit the amount of data being compressed.

Orientation: whether the read aligned as read or as the reverse complement.

Paired Ordination: the orientation of a second read in paired-end sequencing data. In paired-end sequencing, the second read will typically have an opposite orientation as the first read. A paired orientation can be a flag to indicate whether a second read has the same or opposite orientation as the first read.

Unaligned: unaligned reads without any additional encoding.

Length: length of a particular read.

At Step 214 of many embodiments, quality data and/or read identifiers are compressed. In some embodiments preserving read order, the quality data and/or read identifiers are compressed directly, whereas various embodiments that do not preserve read order will reorder the quality scores and/or read identifiers to match the order of the sequencing reads before compressing before compressing the quality scores and/or read identifiers. Various embodiments will utilize known compression methods, including BSC, to compress the quality data and/or read identifiers. In many embodiments, the quality data and/or read identifiers will be compressed in blocks, such as the blocks described in Step 212. Further embodiments will bin quality scores into a reduced set of scores. Some embodiments will implement the binning scheme as designed by Illumina that reduces a quality score system with ≥40 quality scores into 8 bins. (See e.g., www.illumina.com/documents/products/whitepapers/whitepaper_datacompression.pdf.) Binning quality scores can reduce the amount of data to be compressed with minimal impact on the overall breadth of quality data.

Additionally, many read identifiers are arbitrarily generated by sequencing platforms based on factors such as location of a particular molecule during the sequencing process. As such, some embodiments will remove some or all of the read identifiers for the sequencing reads. Further, in embodiments that compress only sequencing data, (e.g., FASTA format), no quality information will exist, and these embodiments will not compress quality data.

At Step 216 of many embodiments, the compressed genetic sequencing data will be converted to a tar archive. Once compressed, certain embodiments will transmit the compressed genetic sequencing data to a remote device, such as a server, computer, or other computing device over a network or series of networks.

The above steps of the flow diagram of FIG. 2 may be executed or performed in an order or sequence not limited to the order and sequence shown and described in FIG. 2. For example, in certain embodiments that preserve the read order, compressing quality data and/or read identifiers Step 214 can be performed at any point after preprocessing step 204, as the order of the read identifiers and/or quality data will not change in intervening Steps 206-212. Additionally, some of the above steps of the flow diagram of FIG. 2 may be executed or performed substantially simultaneously where appropriate. Further, some of the above steps of the flow diagram of FIG. 2 may be omitted, such as transmitting compressed sequencing data or steps involved with paired-end sequencing data, when the obtained sequencing data is single-read sequencing. Additionally, although FIG. 2 is described in relation to a method, it should be noted that many embodiments will be directed to systems comprising a processor and a memory readable by the processor, and instructions in the memory that when read by the processor direct the processor to perform the steps of the method of FIG. 2. Further embodiments will be directed to non-transitory, machine-readable media containing processor instructions, where execution of the instructions by a processor causes the processor to perform the steps of the method of FIG. 2.

Many embodiments are capable of very high levels of compression, as illustrated in Tables 1 and 2. Table 1 illustrates the compression levels of an embodiment that preserves read order as compared to other methods of compressing genetic sequencing data, while Table 2 illustrates the compression levels of an embodiment that does not preserve read order, bins quality scores, and removes arbitrary read identifiers. As illustrated in Table 1, some embodiments are capable of compressing genetic sequencing data to as little as 3% of the uncompressed state. Additionally, certain embodiments represent an improvement over other methods of compressing genetic sequencing data.

TABLE 1

Genetic Sequencing Data Compression - Read Order Preserved

| Dataset | Uncompressed Size | pigz | DSRC 2 | FaStore (fast) | FaStore | Embodiments | Compression Ratio | Versus FaStore (X) |
|---|---|---|---|---|---|---|---|---|
| E. coli | 827 | 253 | 189 | ** | ** | 106 | 13% | |
| P. aeruginosa | 768 | 279 | 198 | 142 | 145 | 115 | 15% | 1.26 |
| S. cerevisiae | 5,986 | 2,062 | 1,507 | ** | ** | 954 | 16% | |
| T. cacao | 13,847 | 4,926 | 3,540 | 2,755 | 2,714 | 2,444 | 18% | 1.11 |
| Metagenomic | 19,284 | 6,911 | 5,155 | 1,628 | 3,602 | 3,206 | 17% | 1.12 |
| PhiX | 50,090 | 6,402 | 6,594 | 1,552 | 1,457 | 1,420 | 3% | 1.03 |
| H. sapiens 1 | 12,861 | 3,920 | 2,702 | 2,293 | 2,299 | 2,118 | 16% | 1.09 |
| H. sapiens 2 | 227,246 | 74,250 | 52,049 | 36,042 | 35,662 | 28,901 | 13% | 1.23 |
| H. sapiens 3 | 195,748 | 36,131 | 26,520 | 11,380 | 11,101 | 6,971 | 4% | 1.59 |
| H. sapiens 4 | 787,616 | 144,927 | 106,665 | 35,129 | 33,734 | 25,883 | 3% | 1.30 |

\* Sizes in MB
\*\* Does not support variable length sequencing data

TABLE 2

Genetic Sequencing Data Compression - Read Order Not Preserved

| Dataset | Uncompressed Size | FaStore (fast) | FaStore | Embodiments | Compression Ratio | Versus FaStore (X) |
|---|---|---|---|---|---|---|
| E. coli | 827 | ** | ** | 63 | 8% | |
| P. aeruginosa | 768 | 83 | 88 | 62 | 8% | 1.42 |
| S. cerevisiae | 5,986 | ** | ** | 366 | 6% | |
| T. cacao | 13,847 | 1,339 | 1,300 | 1,215 | 9% | 1.07 |
| Metagenomic | 19,284 | 1,937 | 1,935 | 1,736 | 9% | 1.11 |
| PhiX | 50,090 | 1,226 | 1,099 | 1,160 | 2% | 0.95 |
| H. sapiens 1 | 12,861 | 1,244 | 1,251 | 1,223 | 10% | 1.02 |
| H. sapiens 2 | 227,246 | 17,846 | 17,417 | 13,460 | 6% | 1.29 |
| H. sapiens 3 | 195,748 | 10,246 | 9,927 | 5,657 | 3% | 1.75 |
| H. sapiens 4 | 787,616 | 30,379 | 28,846 | 20,316 | 3% | 1.42 |

\* Sizes in MB
\*\* Does not support variable length sequencing data

Many embodiments are also capable of reducing time necessary to compress the genetic sequencing data, as illustrated in Table 3. Table 3 illustrates the time to compress various datasets in both embodiments preserving and not preserving read order, where the embodiment not preserving read order also bins quality scores and removes arbitrary read identifiers. As illustrated in Table 3, some embodiments are capable of compressing genetic sequencing data in comparable or less time as other methods. Additionally, certain embodiments represent an improvement over other methods of compressing genetic sequencing data.

TABLE 3

Genetic Sequencing Data Compression Time

| | | | Read Order Preserved | | | Read Order Not Preserved | | |
|---|---|---|---|---|---|---|---|---|
| Dataset | pigz | DSRC 2 | FaStore (fast) | FaStore | Embodiments | FaStore (fast) | FaStore | Embodiments |
| E. coli | 10 s | 2 s | ** | ** | 41 s | ** | ** | 41 s |
| P. aeruginosa | 31 s | 4 s | 35 s | 2 m 2 s | 23 s | 28 s | 1 m 50 s | 27 s |
| S. cerevisiae | 1 m 17 s | 25 s | ** | ** | 3 m 3 s | ** | ** | 2 m 55 s |
| T. cacao | 3 m | 1 m 10 s | 5 m 12 s | 18 m | 9 m | 3 m 30 s | 15 m | 9 m |
| Metagenomic | 4 m 38 s | 1 m 27 s | 7 m | 17 m | 10 m | 5 m | 14 m | 10 m |
| PhiX | 6 m | 2 m 8 s | 13 m | 30 m | 14 m | 11 m | 25 m | 17 m |
| H. sapiens 1 | 2 m 37 s | 36 s | 4 m 37 s | 25 m | 11 m | 3 m 54 s | 24 m | 11 m |
| H. sapiens 2 | 49 m | 13 m | 1 h 19 m | 3 h 35 m | 2 h 30 m | 1 h | 3 h 9 m | 2 h 32 m |
| H. sapiens 3 | 33 m | 9 m | 58 m | 2 h 36 m | 2 h 30 m | 53 m | 2 h 28 m | 2 h 13 m |
| H. sapiens 4 | 2 h 17 m | 43 m | 4 h 10 m | 9 h 51 m | 6 h 39 m | 3 h 50 m | 8 h 52 m | 7 h 33 m |

\*\* Does not support variable length sequencing data

Additional embodiments are also capable of reducing memory necessary to compress the genetic sequencing data, as illustrated in Table 4. Table 4 illustrates the memory used (RAM) in GB used to compress various datasets in embodiments both preserving and not preserving read order, where the embodiment not preserving read order also bins quality scores and removes arbitrary read identifiers. As illustrated in Table 4, some embodiments are capable of compressing genetic sequencing data with less RAM than other methods. Additionally, certain embodiments represent an improvement over other methods of compressing genetic sequencing data.

TABLE 4

Genetic Sequencing Data Compression Memory

| | | | Read Order Preserved | | | Read Order Not Preserved | | |
|---|---|---|---|---|---|---|---|---|
| Dataset | pigz | DSRC 2 | FaStore (fast) | FaStore | Embodiments | FaStore (fast) | FaStore | Embodiments |
| E. coli | 0.008 | 0.13 | ** | ** | 1.4 | ** | ** | 1.1 |
| P. aeruginosa | 0.008 | 0.13 | 2.3 | 2.3 | 1.5 | 2.1 | 2.1 | 0.84 |
| S. cerevisiae | 0.008 | 0.13 | ** | ** | 2.3 | ** | ** | 2.3 |
| T. cacao | 0.008 | 0.13 | 4.2 | 4.1 | 3.3 | 3.4 | 3.6 | 3.7 |
| Metagenomic | 0.008 | 0.13 | 11 | 11 | 3.6 | 9.3 | 9.2 | 5.0 |

TABLE 4-continued

Genetic Sequencing Data Compression Memory

| Dataset | pigz | DSRC 2 | Read Order Preserved | | | Read Order Not Preserved | | |
| --- | --- | --- | --- | --- | --- | --- | --- | --- |
| | | | FaStore (fast) | FaStore | Embodiments | FaStore (fast) | FaStore | Embodiments |
| PhiX | 0.008 | 0.12 | 25 | 26 | 18 | 20 | 24 | 21 |
| H. sapiens 1 | 0.008 | 0.18 | 17 | 18 | 4.9 | 13 | 14 | 5.3 |
| H. sapiens 2 | 0.008 | 0.42 | 35 | 31 | 45 | 25 | 26 | 45 |
| H. sapiens 3 | 0.008 | 0.13 | 40 | 41 | 32 | 38 | 32 | 31 |
| H. sapiens 4 | 0.008 | 0.15 | 158 | 137 | 119 | 145 | 122 | 119 |

\* Memory (RAM) in GB
\*\* Does not support variable length sequencing data

Sequence Data Decompression

Figure 3:
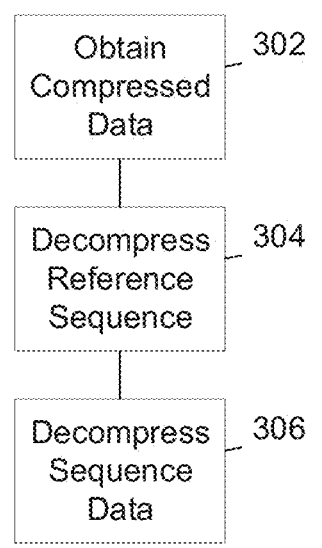
FIG. 3 illustrates a method for decompressing genetic sequencing data in accordance with various embodiments.

Turning now to FIG. 3, a method for decompressing compressed genetic sequencing data is illustrated. At step 302, compressed genetic sequencing data is obtained. In certain embodiments, the compressed genetic sequencing data is data stored or archived locally, while additional embodiments will obtain the compressed genetic sequencing data from a remote device, such as a server, computer, or other computing device connected across a network or series of networks.

At Step 304, a reference sequence is decompressed from the compressed genetic sequencing data. Once a reference sequence is decompressed, the remaining compressed genetic sequencing data is decompressed at Step 306 of a number of embodiments. In embodiments where the compressed genetic sequencing data is stored in blocks, individual blocks are decompressed in parallel, sequentially, or as selected by a user (e.g., a user can select to decompress only specific blocks). When decompressing the compressed genetic sequencing data, the various streams (e.g., the streams described in relation to FIG. 2) stored in the compressed genetic sequencing data identify the sequences of individual reads.

The above steps of the flow diagram of FIG. 3 may be executed or performed in an order or sequence not limited to the order and sequence shown and described in FIG. 3. Some of the above steps of the flow diagram of FIG. 3 may be executed or performed substantially simultaneously where appropriate. Additionally, some of the above steps of the flow diagram of FIG. 3 may be omitted in some embodiments. Additionally, although FIG. 3 is described in relation to a method, it should be noted that many embodiments will be directed to systems comprising a processor and a memory readable by the processor, and instructions in the memory that when read by the processor direct the processor to perform the steps of the method of FIG. 3. Further embodiments will be directed to non-transitory, machine-readable media containing processor instructions, where execution of the instructions by a processor causes the processor to perform the steps of the method of FIG. 3.

Many embodiments are also capable of reducing time and memory necessary to decompress the genetic sequencing data, as illustrated in Tables 5 and 6. Table 5 illustrates the time to decompress various datasets in embodiments both preserving and not preserving read order, while Table 6 illustrates the memory used (RAM) in GB used to decompress various datasets in embodiments both preserving and not preserving read order. As illustrated in Table 5, some embodiments are capable of decompressing genetic sequencing data in comparable or less time as other methods, and Table 6 illustrates that some embodiments are capable of decompressing genetic sequencing data with less RAM than other methods. Additionally, certain embodiments represent an improvement over other methods of compressing genetic sequencing data.

TABLE 5

Genetic Sequencing Data Decompression Time

| Dataset | pigz | DSRC 2 | Read Order Preserved | | | Read Order Not Preserved | | |
| --- | --- | --- | --- | --- | --- | --- | --- | --- |
| | | | FaStore (fast) | FaStore | Embodiments | FaStore (fast) | FaStore | Embodiments |
| E. coli | 3 s | 2 s | \*\* | \*\* | 17 s | \*\* | \*\* | 15 s |
| P. aeruginosa | 4.000 | 2 s | 12 s | 18 s | 9 s | 7 s | 12.0 | 7 s |
| S. cerevisiae | s27 s | 10 s | \*\* | \*\* | 1 m | \*\* | \*\* | 43 s |
| T. cacao | 1 m 13 s | 23 s | 2 m 5 s | 2 m 14 s | 2 m 20 s | 1 m 9 s | 1 m 11 s | 1 m 46 s |
| Metagenomic | 1 m 46 s | 37 s | 2 m 42 s | 3 m | 3 m 18 s | 1 m 21 s | 1 m 36 s | 2 m 29 s |
| PhiX | 2 m 23 s | 39 s | 3 m 3 s | 3 m 47 s | 5 m 32 s | 2 m 33 s | 2 m 11 s | 5 m 34 s |
| H. sapiens 1 | 1 m | 18 s | 1 m 27 s | 1 m 39 s | 2 m 25 s | 58 s | 59 s | 2 m 29 s |
| H. sapiens 2 | 20 m | 14 m | 24 m | 25 m | 38 m | 15 m | 16 m | 28 m |
| H. sapiens 3 | 11 m | 9 m | 11 m | 12 m | 26 m | 9 m | 10 m | 22 m |
| H. sapiens 4 | 1 h 21 m | 41 m | 40 m | 45 m | 1 h 47 m | 32 m | 36 m | 1 h 37 m |

\*\* Does not support variable length sequencing data

TABLE 6

Genetic Sequencing Data Decompression Memory

| Dataset | pigz | DSRC 2 | Read Order Preserved | | | Read Order Not Preserved | | |
| --- | --- | --- | --- | --- | --- | --- | --- | --- |
| | | | FaStore (fast) | FaStore | Embodiments | FaStore (fast) | FaStore | Embodiments |
| E. coli | 0.003 | 0.23 | ** | ** | 1.7 | ** | ** | 1.7 |
| P. aeruginosa | 0.003 | 0.24 | 0.78 | 0.8 | 1.7 | 0.53 | 0.61 | 1.7 |
| S. cerevisiae | 0.003 | 0.43 | ** | ** | 2.2 | ** | ** | 1.9 |
| T. cacao | 0.003 | 0.29 | 1.7 | 2.3 | 2.1 | 1.2 | 1.5 | 1.7 |
| Metagenomic | 0.003 | 0.29 | 1.9 | 1.9 | 2.6 | 1.3 | 1.4 | 3.1 |
| PhiX | 0.003 | 0.33 | 19 | 16 | 2.3 | 15 | 13 | 2.3 |
| H. sapiens 1 | 0.003 | 0.30 | 2 | 1.7 | 3.2 | 1.4 | 1.3 | 3.7 |
| H. sapiens 2 | 0.003 | 0.42 | 26 | 19 | 5.5 | 21 | 15 | 5.5 |
| H. sapiens 3 | 0.003 | 0.34 | 39 | 23 | 6.1 | 30 | 17 | 3.3 |
| H. sapiens 4 | 0.003 | 0.36 | 141 | 85 | 6.6 | 110 | 81 | 6.7 |

*Memory (RAM) in GB
** Does not support variable length sequencing data

Long Read Compression

Many embodiments are capable of compressing genetic sequencing data arising from long-read sequencing (e.g., Pacific Biosciences). While many sequencing platforms (e.g., Illumina) are generally limited to 150-250 base pair reads, Pacific Biosciences platforms can produce read lengths above 10,000 base pairs in length. Table 7 illustrates the compression efficiency of an embodiment performed on genetic sequencing data arising from Pacific Biosciences and Oxford Nanopore sequencing platforms from samples of *Escherichia coli*. As seen, in Table 7, certain embodiments are capable of compressing long read genetic sequencing data to a level of approximately 30% of the uncompressed size. Additionally, certain embodiments provide an improvement over other methods.

TABLE 7

Long Read Compression

| Species | Platform | Genome Size (Mbp) | Max. Read Length | # Reads (M) | Coverage | Uncompressed Size | pigz | Embodiments | Compress Ratio | Versus pigz (X) |
| --- | --- | --- | --- | --- | --- | --- | --- | --- | --- | --- |
| E. coli | PacBio | 4.6 | 49,424 | 0.65 | 140x | 1,304 | 546 | 420 | 32% | 1.3 |
| E. coli | Ox Nano | 4.6 | 47,422 | 0.08 | 86x | 264 | 120 | 94 | 36% | 1.3 |

*size in MB

Doctrine of Equivalents

Although specific methods of compressing genetic sequencing data are discussed above. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for compressing genetic sequencing data, comprising:
    obtaining genetic sequencing data containing a plurality of sequencing reads from a high-throughput sequencing platform;
    reordering the plurality of sequencing reads from the genetic sequencing data based on homology between sequencing reads in the plurality of sequencing reads, wherein the plurality of sequencing reads comprises 10,000 unique sequencing reads;
    encoding the plurality of sequencing reads based on a relative position of each sequencing read to the reordered plurality of sequencing reads, wherein a comprehensive sequence is yielded from contigs of the sequences of the reordered plurality of sequencing reads, wherein each sequencing read has an alignment to the comprehensive sequence at its relative position within the reordered plurality of sequencing reads such that its sequencing read position is based on contiguity with a previous sequencing read within the reordered plurality of sequencing reads and not based on alignment to the comprehensive sequence such that encoding is performed without referential sequence alignment;
    generating a plurality of data streams describing characteristics about each sequencing read in the plurality of sequencing reads, wherein each characteristic data stream is reordered based on the position of the sequencing read it characterizes such that the order of the plurality of characteristic data stream matches the order of the reordered plurality of sequencing reads; and
    compressing the reordered plurality of sequencing reads and the reordered plurality of characteristic data streams, wherein the reordered plurality of sequencing reads is compressed separately from the reordered plurality of characteristic data streams.

2. The method of claim 1, wherein the compressing step is performed in a series of blocks representing an additional subset of sequencing reads in the plurality of sequencing reads.

3. The method of claim 1, wherein the genetic sequencing data represents paired-end sequencing data containing a plurality of paired sequencing reads, wherein each pair of sequencing reads contains a first read and a second read, where the first read represents one end of a sequenced molecule, and the second read represents an opposite end of the sequenced molecule.

4. The method of claim 3, wherein the position of first read of each paired sequencing read is utilized to determine the relative position of the paired sequencing read within the reordered plurality of reads and the position of the second read of each paired sequencing read within the reordered plurality of reads is based on its position relative to its paired first read.

5. The method of claim 1, further comprising transmitting the compressed reordered plurality of sequencing reads to a remote device.

6. The method of claim 1, wherein the characteristic data includes quality data for each sequencing read in the plurality of sequencing reads.

7. A system for compressing genetic sequencing data, comprising:
   a processor;
   a memory readable by the processor; and
   instructions in the memory that when read by the processor direct the processor to:
      obtain genetic sequencing data containing a plurality of sequencing reads from a high-throughput sequencing platform;
      reorder the plurality of sequencing reads from the genetic sequencing data based on homology between sequencing reads in the plurality of sequencing reads, wherein the plurality of sequencing reads comprises 10,000 unique sequencing reads;
      encode the plurality of sequencing reads based on a relative position of each sequencing read to the reordered plurality of sequencing reads wherein a comprehensive sequence is yielded from contigs of the sequences of the reordered plurality of sequencing reads, wherein each sequencing read has an alignment to the comprehensive sequence at its relative position within the reordered plurality of sequencing reads such that its sequencing read position is based on contiguity with a previous sequencing read within the reordered plurality of sequencing reads and not based on alignment to the comprehensive sequence such that encoding is performed without referential sequence alignment;
      generate a plurality of data streams describing characteristics about each sequencing read in the plurality of sequencing reads, wherein each characteristic data stream is reordered based on the position of the sequencing read it characterizes such that the order of the plurality of characteristic data stream matches the order of the reordered plurality of sequencing reads; and
      compress the reordered plurality of sequencing reads and the reordered plurality of characteristic data streams, wherein the reordered plurality of sequencing reads is compressed separately from the reordered plurality of characteristic data streams.

8. The system of claim 7, wherein the instructions further direct the processor to compress the plurality of sequencing reads in a series of blocks representing an additional subset of sequencing reads in the plurality of sequencing reads.

9. The system of claim 7, wherein the genetic sequencing data represents paired-end sequencing data containing a plurality of paired sequencing reads, wherein each pair of sequencing reads contains a first read and a second read, where the first read represents one end of a sequenced molecule, and the second read represents an opposite end of the sequenced molecule.

10. The system of claim 9, wherein the position of first read of each paired sequencing read is utilized to determine the relative position of the paired sequencing read within the reordered plurality of reads and the position of the second read of each paired sequencing read within the reordered plurality of reads is based on its position relative to its paired first read.

11. The system of claim 7, wherein the instructions further direct the processor to transmit the compressed reordered plurality of sequencing reads to a remote device.

12. The system of claim 7, wherein the characteristic data includes quality data for each sequencing read in the plurality of sequencing reads.

13. A non-transitory, machine-readable medium containing processor instructions, where execution of the instructions by a processor causes the processor to perform a process to compressing genetic sequencing data comprising:
   obtaining genetic sequencing data containing a plurality of sequencing reads from a high-throughput sequencing platform;
   reordering the plurality of sequencing reads from the genetic sequencing data based on homology between sequencing reads in the plurality of sequencing reads, wherein the plurality of sequencing reads comprises 10,000 unique sequencing reads;
   encoding the plurality of sequencing reads based on a relative position of each sequencing read to the reordered plurality of sequencing reads wherein a comprehensive sequence is yielded from contigs of the sequences of the reordered plurality of sequencing reads, wherein each sequencing read has an alignment to the comprehensive sequence at its relative position within the reordered plurality of sequencing reads such that its sequencing read position is relative to based on contiguity with a previous sequencing read within the reordered plurality of sequencing reads and not based on alignment to the comprehensive sequence such that encoding is performed without referential sequence alignment;
   generating a plurality of data streams describing characteristics about each sequencing read in the plurality of sequencing reads, wherein each characteristic data stream is reordered based on the position of the sequencing read it characterizes such that the order of the plurality of characteristic data stream matches the order of the reordered plurality of sequencing reads; and
   compressing the reordered plurality of sequencing reads and the reordered plurality of characteristic data streams, wherein the reordered plurality of sequencing reads is compressed separately from the reordered plurality of characteristic data streams.

14. The non-transitory, machine-readable medium of claim 13, wherein the compressing step is performed in a series of blocks representing an additional subset of sequencing reads in the plurality of sequencing reads.

15. The non-transitory, machine-readable medium of claim 13, wherein the genetic sequencing data represents paired-end sequencing data containing a plurality of paired sequencing reads, wherein each pair of sequencing reads contains a first read and a second read, where the first read represents one end of a sequenced molecule, and the second read represents an opposite end of the sequenced molecule.

16. The non-transitory, machine-readable medium of claim 15, wherein the position of first read of each paired sequencing read is utilized to determine the relative position of the paired sequencing read within the reordered plurality of reads and the position of the second read of each paired sequencing read within the reordered plurality of reads is based on its position relative to its paired first read.

17. The non-transitory, machine-readable medium of claim 13, wherein the instructions further comprise transmitting the compressed reordered plurality of sequencing reads to a remote device.

18. The non-transitory, machine-readable medium of claim 13, wherein the characteristic data includes quality data for each sequencing read in the plurality of sequencing reads.

* * * * *